US010413232B2

(12) United States Patent
Stamnes

(10) Patent No.: US 10,413,232 B2
(45) Date of Patent: Sep. 17, 2019

(54) OPTICAL TRANSFER DIAGNOSIS FOR DETECTION AND MONITORING OF TISSUE DISORDERS

(71) Applicant: Balter, Inc., Maplewood, NJ (US)

(72) Inventor: Jakob J. Stamnes, Oslo (NO)

(73) Assignee: BALTER MEDICAL, AS., Bergen (NO)

( * ) Notice: Subject to any disclaimer, the term of this patent is extended or adjusted under 35 U.S.C. 154(b) by 94 days.

(21) Appl. No.: 15/430,019

(22) Filed: Feb. 10, 2017

(65) Prior Publication Data

US 2017/0224270 A1    Aug. 10, 2017

Related U.S. Application Data

(60) Provisional application No. 62/293,579, filed on Feb. 10, 2016.

(51) Int. Cl.
*G06K 9/00* (2006.01)
*A61B 5/00* (2006.01)
(Continued)

(52) U.S. Cl.
CPC ............ *A61B 5/444* (2013.01); *A61B 5/0077* (2013.01); *A61B 5/1075* (2013.01); *A61B 5/1079* (2013.01); *A61B 5/14546* (2013.01); *A61B 5/14551* (2013.01); *A61B 5/443* (2013.01); *G06K 9/00127* (2013.01); *G06K 9/00664* (2013.01); *G06K 9/209* (2013.01); *G06K 9/2018* (2013.01); *G06K 9/228* (2013.01); *G06K 9/4661* (2013.01); *G06K 9/525* (2013.01); *G06K 9/54* (2013.01); *G06K 9/6218* (2013.01);
(Continued)

(58) Field of Classification Search
CPC ........ A61B 2562/0233; A61B 2576/02; A61B 5/0077; A61B 5/1075; A61B 5/1079; A61B 5/14546; A61B 5/14551; A61B 5/443; A61B 5/444; G06K 9/6262; G06K 9/00127; G06K 2209/05; G06K 9/00664; G06K 9/2018; G06K 9/209; G06K 9/228; G06K 9/4661; G06K 9/525; G06K 9/54; G06K 9/6218; G06K 9/6234; G06T 7/0012; G06T 2207/10024; G06T 2207/30088; G06T 2207/30096
See application file for complete search history.

(56) References Cited

U.S. PATENT DOCUMENTS

2003/0236458 A1    12/2003  Hochman
2004/0092824 A1*  5/2004  Stamnes .............. A61B 5/0062
                                              600/473
(Continued)

OTHER PUBLICATIONS

International Search Report and Written Opinion of the International Searching Authority dated May 19, 2017 for International Application No. PCT/US2017/017450 (14 Pages).

*Primary Examiner* — Tom Y Lu
(74) *Attorney, Agent, or Firm* — Brown Rudnick LLP

(57) ABSTRACT

Systems and methods for discriminating between malignant and benign pigmented skin lesions based on optical analysis using spatial distribution maps, morphological parameters, and additional diagnostic parameters derived from images of tissue lesions. A handheld optical transfer diagnosis device is disclosed capable of capturing a series of reflectance images of a skin lesion at a variety of angles of illumination and observation.

13 Claims, 11 Drawing Sheets

(51) Int. Cl.
  *A61B 5/107* (2006.01)
  *A61B 5/145* (2006.01)
  *A61B 5/1455* (2006.01)
  *G06K 9/22* (2006.01)
  *G06K 9/46* (2006.01)
  *G06K 9/54* (2006.01)
  *G06K 9/62* (2006.01)
  *G06K 9/20* (2006.01)
  *G06K 9/52* (2006.01)
  *G06T 7/00* (2017.01)

(52) U.S. Cl.
  CPC ......... *G06K 9/6234* (2013.01); *G06K 9/6262* (2013.01); *G06T 7/0012* (2013.01); *A61B 2562/0233* (2013.01); *A61B 2576/02* (2013.01); *G06K 2209/05* (2013.01); *G06T 2207/10024* (2013.01); *G06T 2207/30088* (2013.01); *G06T 2207/30096* (2013.01)

(56) References Cited

U.S. PATENT DOCUMENTS

| | | |
|---|---|---|
| 2007/0269804 A1* | 11/2007 | Liew .................. G06F 19/24 435/6.11 |
| 2011/0054298 A1 | 3/2011 | Stamnes et al. |
| 2012/0136255 A1 | 5/2012 | Fan et al. |
| 2013/0322711 A1 | 12/2013 | Schultz et al. |
| 2014/0036054 A1* | 2/2014 | Zouridakis ............ G06T 7/0012 348/77 |
| 2015/0297130 A1 | 10/2015 | Stamnes et al. |

* cited by examiner

OPTICAL TRANSFER DIAGNOSIS FOR DETECTION AND MONITORING OF TISSUE DISORDERS

CROSS REFERENCE TO RELATED CASES

This application claims priority to U.S. Provisional Application Ser. No. 62/293,579, filed Feb. 10, 2016.

FIELD OF THE INVENTION

The present disclosure relates to a method for discriminating between different types of tissue lesions. In particular, the present disclosure is directed to a method for discriminating between malignant and benign tissue lesions.

BACKGROUND

Malignant melanoma is one of the most rapidly increasing cancers in the world. Successful treatment of melanoma depends on early detection by clinicians with subsequent surgical removal of tumors. In recent years, considerable effort has been expended on developing optical methods for characterizing tissue and monitoring changes. In 2014, the Canadian Agency for Drugs and Technologies in Health published a report on optical scanners for melanoma detection, discussing three different devices (Aura, MelaFind, and SIMSYS-MoleMate) approved for marketing in Canada and/or USA. See V. Foerster, "Optical scanners for melanoma detection" [Issues in emerging health technologies, Issue 123]. Ottawa: Canadian Agency for Drugs and Technologies in Health (2014), incorporated herein by reference. As the report confirms, the 5-year survival rate is 93 to 97% for melanoma detected at an early stage, but drops to between 10 and 20% for advanced stage detection, implying that there is a need for accurate diagnostic devices to enable early detection while avoiding unnecessary biopsies. The devices profiled included Aura (Verisante Technology, Inc., Vancouver, British Columbia, Canada), MelaFind (MELA Sciences, Inc., Irvington, N.Y., USA), and SIMSYS-MoleMate Skin Imaging System (MedX Health, Inc., Hamilton, Ontario, Canada).

Aura utilizes near-infrared laser light and Raman spectroscopy to distinguish malignant from benign skin lesions and has shown sensitivities ranging from 90 to 99% for specificities ranging from 58 to 15% for discriminating between benign and malignant lesions.

MelaFind illuminates the skin at 10 wavelengths, measures light scattered back from the skin, and uses image analysis algorithms combined with a skin disorder database to provide treatment suggestion. For discrimination between melanoma and benign pigmented lesions in a population of suspicious lesions, MelaFind showed 98% sensitivity and 9% specificity in a clinical study involving 1,383 patients with 1,831 pigmented skin lesions.

SIMSYS-MoleMate Skin Imaging System is based on using a handheld, multispectral scanner and computer software to provide dermatoscopic images, dermal and epidermal pathological characteristics, and the ability to catalogue, monitor, and compare lesions over time. In a randomized controlled trial involving 1,297 patients with 1,580 suspicious pigmented lesions it was found that adding MoleMate to best practices resulted in lower agreement with expert assessment that the lesion was benign and led to a higher proportion of referrals.

Because so much is at stake with regard to early detection and treatment of cancerous skin lesions, the sensitivity and specificity numbers of the existing optical analysis devices leave room for improvement.

SUMMARY

Systems and methods of the invention relate to discriminating between benign and malignant tissue lesions. The present invention provides tools for skin lesion analysis using an optical transfer diagnosis (OTD) system to capture images in cooperation with data processing systems that assign numeric values to a number of lesion characteristics indicative of malignancy. According to certain embodiments, morphological parameters and spatial distribution maps of physiological properties and morphological parameters may be derived from images of tissue lesions that may be obtained using an OTD device, a dermatoscope, digital camera, or the camera of a mobile device such as a smart phone. The various parameters may be weighted and analyzed to provide a diagnostic index indicative of malignancy. The weights may be determined through a cluster analysis of a number of images of lesions having known diagnoses. The diagnostic index tools of the invention, once trained on a sufficiently large data set, allow for diagnosis of malignant tumors with significantly improved specificity and sensitivity over the existing optical analysis techniques. Accordingly, the systems and methods of the invention provide an important diagnostic tool for primary care providers to identify malignant lesions in need of prompt treatment while avoiding unnecessary biopsies, reducing costs and discomfort while increasing survival rates through early detection.

According to certain aspects, the invention provides a method for discriminating between benign and malignant skin lesions. Steps of the method include generating an image of a skin lesion; creating, for each of a plurality of physiological properties and morphological parameters, a spatial distribution map covering the area of the skin lesion from the plurality of spectral reflectance images; determining entropy values for each of the spatial distribution maps; determining cross entropy values between pairs of the spatial distribution maps; determining, from an image, a plurality of morphological parameters; deriving, from the spatial distribution maps, a plurality of additional diagnostic parameters; creating one or more diagnostic indices from the weighted sum of the entropy values, the cross entropy values, and the plurality of morphological parameters, and the plurality of additional diagnostic parameters using one or more weight vectors; determining for each of the one or more diagnostic indices, a reliability value for classification as benign and a reliability value for classification as malignant; and classifying the skin lesion as benign when the reliability value for classification as benign is greater than the reliability value for classification as malignant.

According to certain embodiments, the plurality of physiological properties and morphological parameters may comprise percentage of hemoglobin concentration; percentage of hemoglobin oxygenation; upper epidermal thickness; lower epidermal thickness; percentage of melanosome concentration in upper epidermis; percentage of melanosome concentration in lower epidermis; or percentage of keratin concentration.

The morphological parameters can include size; histogram width; fractal dimension; moment of inertia; asphericity; center distance; border length; average darkness; area divided by fractal dimension; or border length divided by fractal dimension.

In some embodiments, the additional diagnostic parameters may comprise maximum value of melanin optical depth; architectural disorder; blood filling; angiogenesis; ratio of blood oxygenation in an area surrounding a lesion border; melanin contrast; blood contrast; high spatial Fourier-components of a map of total melanin optical depth over a lesion area; and entropy of contrast of the map of total melanin optical depth over the lesion area.

The one or more weight vectors may be determined using clustering analysis of a plurality of pigmented images of skin lesions known to be benign or malignant. The plurality of physiological properties and morphological parameters and the plurality of morphological parameters may constitute a set of generalized diagnostic parameters.

In various embodiments, the image of the skin lesion may be generated using an optical transfer diagnosis (OTD) system comprising a handheld OTD unit in communication with a computing device; a dermatoscope, a smart phone, a tablet, or a digital camera. Methods of the invention may include pre-processing the image of the skin lesion and/or estimating noise using one or more additional images of the skin lesion.

Aspects of the invention may include an optical transfer diagnosis (OTD) system comprising a handheld OTD unit comprising an observation window, which may be placed in contact with the skin during measurement; an illuminating system configured to illuminate a skin lesion through the observation window from a plurality of angles; and an imaging system configured to capture reflectance images of a skin lesion through the observation from a plurality of angles. OTD systems may include a computing device in communication with the handheld OTD unit, the computing device comprising a tangible, non-transient memory coupled to a processor and configured to store the captured reflectance images.

In certain embodiments, OTD systems or dermato scopes may include a docking station configured to receive the handheld OTD unit and comprising a calibration target for calibration of the handheld OTD unit or dermatoscope; and the OTD system or dermatoscope may include an accessory attachment for calibration and automatic performance of function testing before operation. The illuminating system may include fixed light-emitting diode (LED) lamps (1, 2, 3, 4, 5, 6, 7, 8, 9, 10, 11, 12, 13, 14, 15, or as many as 30) at different wavelengths, where each LED lamp is positioned at a different illumination angle relative to the observation window. In certain embodiments, 10 fixed LEDs are used. In other embodiments, 12 fixed LEDs are used. The illumination angles are between about 30 and about 45 degrees with relative azimuth angles between about 34 and about 145 degrees.

In certain embodiments the imaging system may comprise one or more correcting lenses, a camera sensor comprising an IEEE (Institute of Electrical and Electronics Engineers) 1394 FireWire camera, and five mirrors configured to provide a plurality of angles of observation relative to the observation window. The plurality of angles of observation may be between about 0 and about 45 degrees with relative azimuth angles between 0 and 180 degrees.

In certain embodiments the imaging system may comprise one or more correcting lenses, a camera sensor at nadir observation, and an illuminating system including 30 fixed light-emitting diode (LED) lamps at 10 different wavelengths, each wavelength comprising three LED lamps that illuminate the lesion through the observation window from three different directions.

BRIEF DESCRIPTION OF THE FIGURES

The objects and features of the present disclosure, which are believed to be novel, are set forth with particularity in the appended claims. The present disclosure, both as to its organization and manner of operation, together with further objectives and advantages, may be best understood by reference to the following description, taken in connection with the accompanying drawings as set forth below:

DETAILED DESCRIPTION

The present invention relates to systems and methods for discriminating between different types of tissue lesions. In particular, the present invention is directed to optical systems and methods for discriminating between malignant and benign tissue lesions.

In certain embodiments, an optical transfer device is used to image a tissue lesion for analysis. An optical transfer diagnosis (OTD) device, according to certain embodiments, is a spectral radiometer that records a set of 30 images, constituting a lesion measurement, in less than 10 seconds. Images are recorded at 10 different wavelengths (from about 365-about 880 nm) from multiple angles of illumination and detection.

Figure 1:
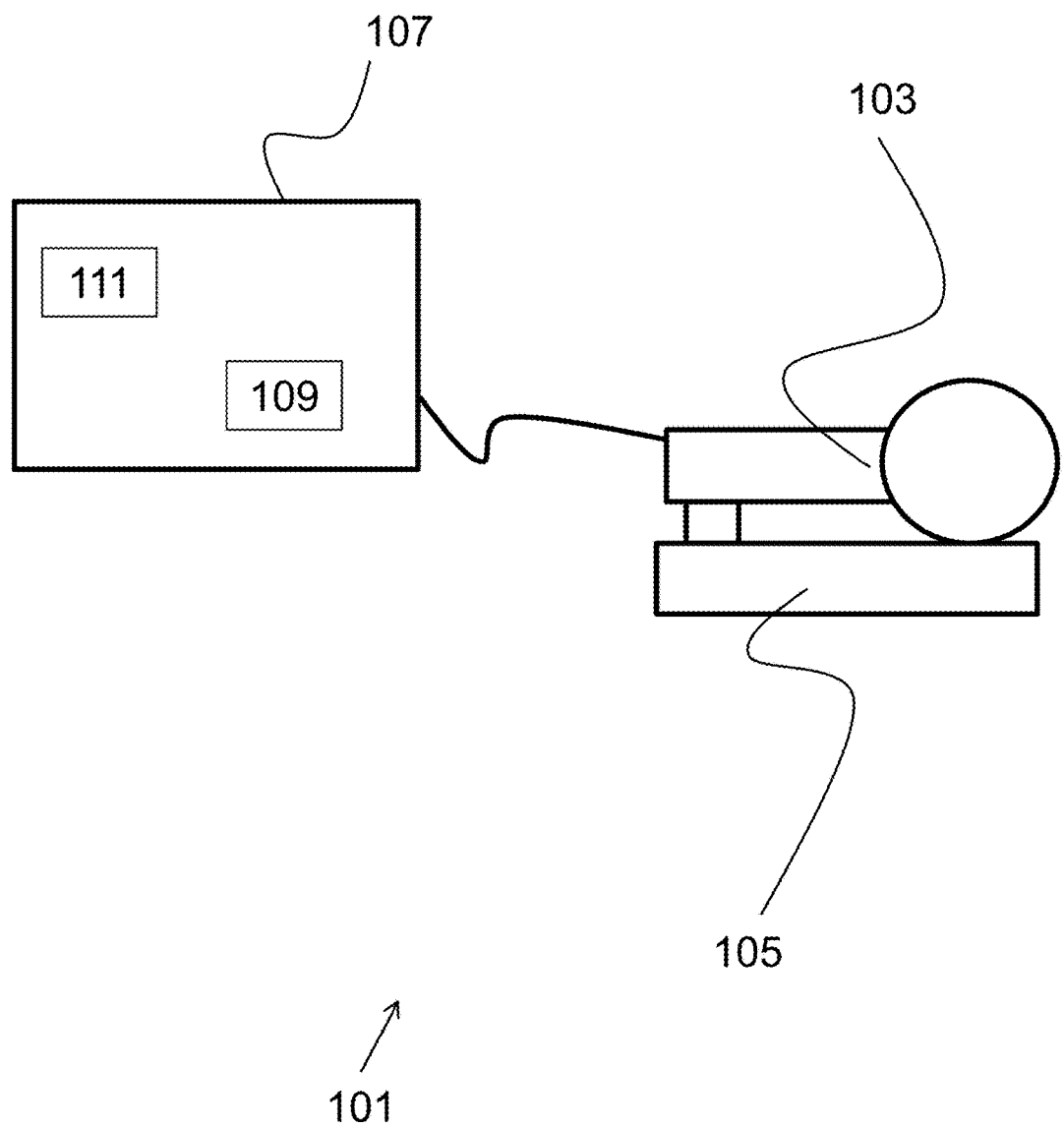
FIG. 1 shows an OTD system with its handheld unit placed in a docking station and connected to a computing device.

As shown in FIG. 1, the OTD system 101 may consist of a handheld unit 103, a docking station 105, and a laptop PC or other computing device 107 comprising a processor 109 coupled to a tangible, non-transient memory 111. The handheld unit 103 may include a release button to initiate image recording. Other controls may be performed via a user interface on the attached computing device 107. When not in use, the handheld unit 103 is placed in the docking station 105, where the observation window of the device is placed against a calibration target.

Figure 2:
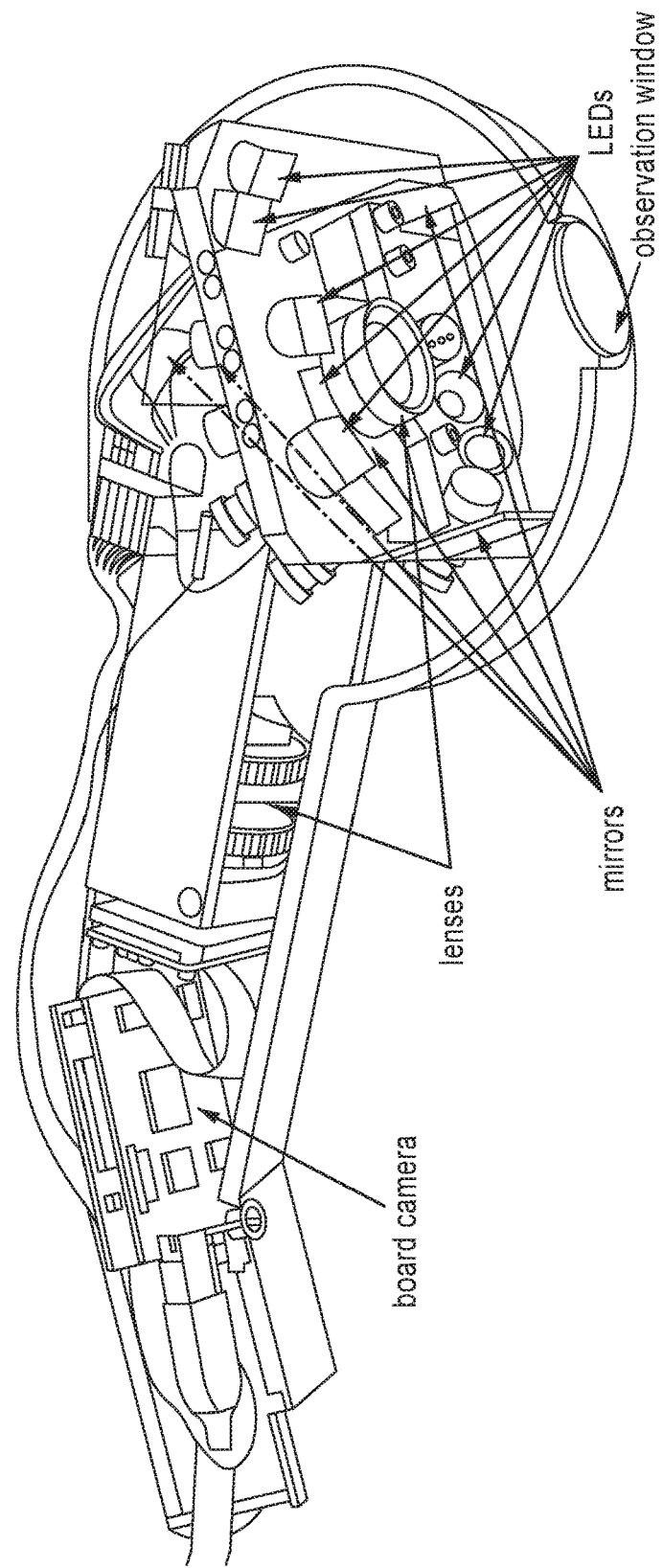
FIG. 2 shows the inner parts of an OTD handheld unit according to certain embodiments.
Figure 3:
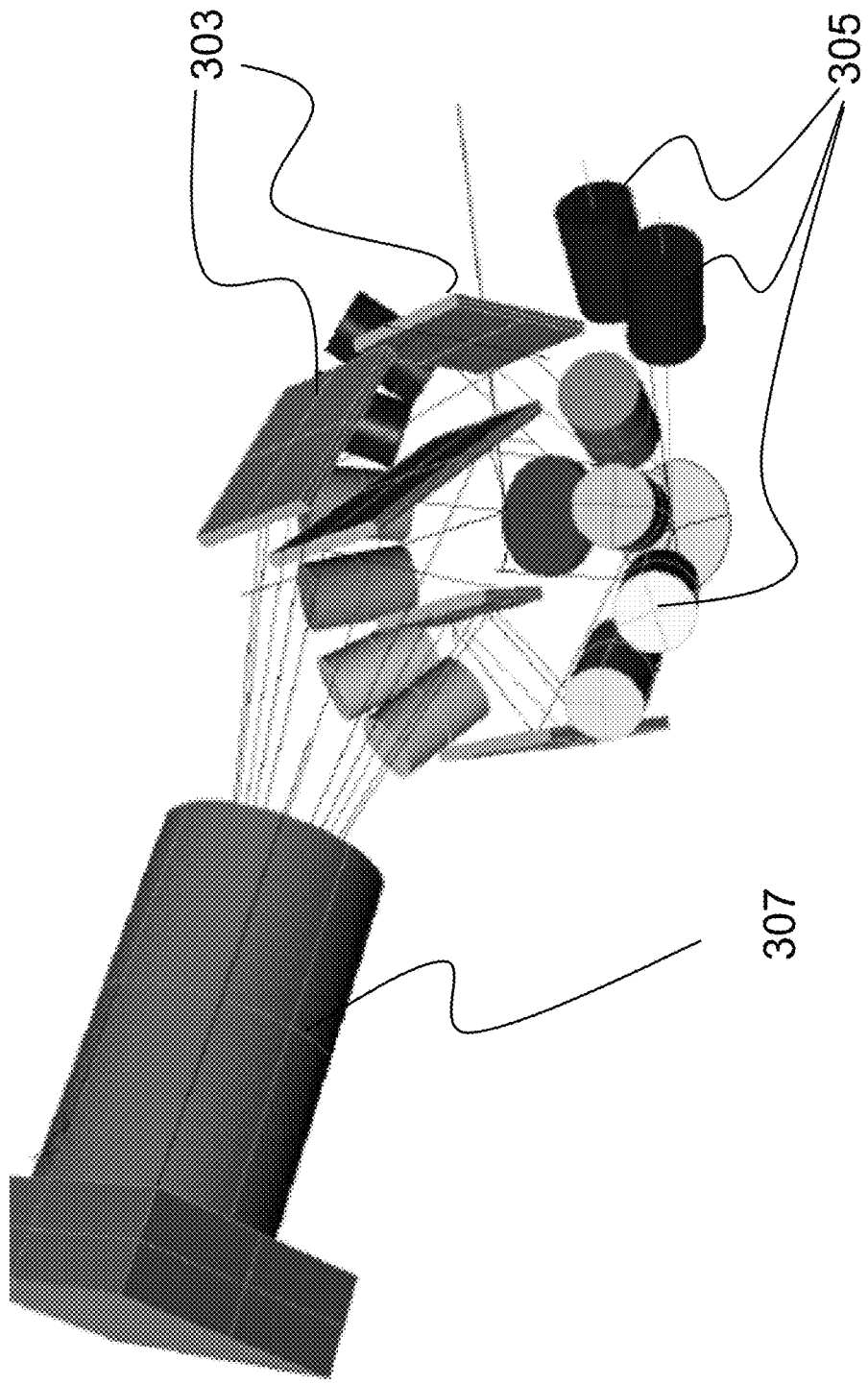
FIG. 3 shows orientation of some of the inner parts of an OTD handheld unit according to certain embodiments.

FIG. 2 shows the inner parts of an exemplary handheld OTD unit. A sensor head may contain an illuminating system consisting of, for example, 12 LED or other light-providing devices 305 and an imaging system comprising at least one camera 307 and a series of mirrors 303, as shown in FIG. 3.

An exemplary illuminating system shown consists of 12 fixed light-emitting diode (LED) lamps. Each LED is placed at a different angle relative to the skin to enhance the ability to retrieve depth information. The polar angles of the LEDs vary between 30 and 45 degrees and the relative azimuth angles between 34 and 145 degrees. The polar angles for the detectors vary between 0 and 45 degrees, and the relative azimuth angles between 0 and 180 degrees.

An exemplary imaging system for a handheld OTD device consists of one correcting lens placed inside the handle plus another correcting lens and five mirrors placed inside a sensor head and a sapphire glass observation window that contacts the area of the skin lesion. OTD devices may comprise a camera sensor consisting of, for example, an IEEE (Institute of Electrical and Electronics Engineers) 1394 FireWire camera.

Figure 4:
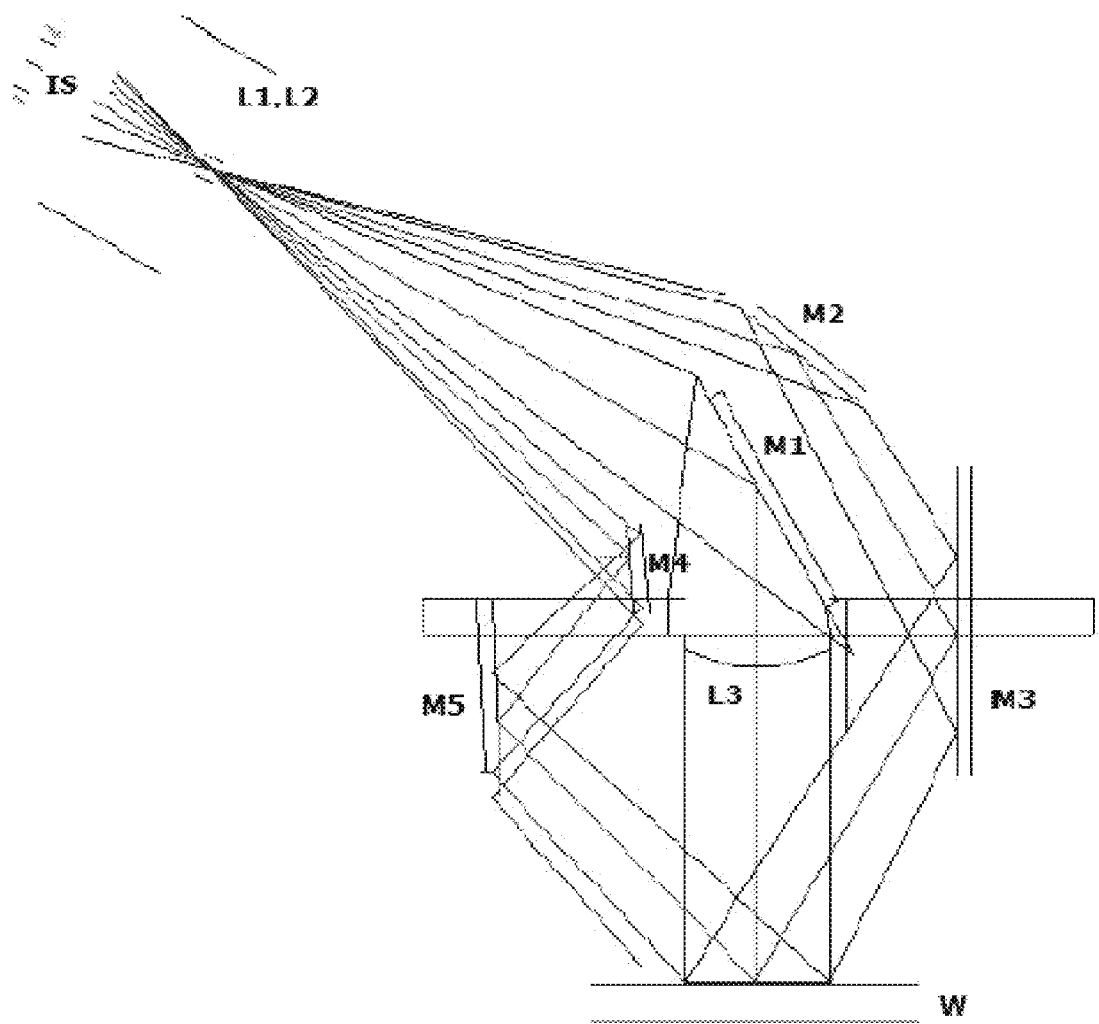
FIG. 4 shows a ray trace of the OTD imaging system according to certain embodiments.

As indicated in FIG. 4, the five mirrors may be used to image the same area of the skin viewed from three different angles on three different sections of the camera sensor. To compensate for different object distances for the three angular views, the camera sensor may be slightly tilted relative to the optical axis. FIG. 4 illustrates a ray trace of the OTD imaging system according to certain embodiments, where IS: Image sensor; L1: Camera lens; L2: Correcting lens 1; L3: Correcting lens 2; M1: Plane mirror for central view image; M2, M3: Plane mirrors for upper 30 degree oblique image; M4, M5: Plane mirrors for lower 45 degree oblique image; and W: Sapphire glass window.

An alcohol-based gel interface may be used where the sapphire observation window contacts the skin to provide refractive-index matching and avoid rough-surface scattering, and to obtain illumination and imaging of a selected area of the skin through the circular sapphire observation window. In preferred embodiments, the observation window may be between about 1.5 and about 5 cm in diameter and may be, for example, about 2 cm.

In certain embodiments, images for analysis using methods of the invention may be obtained using imaging devices such as a dermatoscope, digital camera, smartphone, or tablet. Single or multiple images may be obtained for analysis and, where multiple images are obtained, they may be obtained at different angles of illumination and detection. Where images are obtained using a dermatoscope, digital camera or a mobile device including a camera (e.g., mobile phone or tablet with camera and LED or other source of illumination or flash), the device may prompt a user, via a program stored on a non-transient, tangible memory, to capture a series of images at prescribed orientations relative to a lesion. In certain embodiments, the device camera and/or orienting devices such as gyroscopic or global positioning system features of the device may be used to determine orientation of the camera and light source with respect to the lesion. The imaging device may be configured to determine when the desired orientation has been achieved and to automatically capture an image or series of images or prompt a user to capture the image once the appropriate orientation is reached. Each image may be tagged by the device with the angles of illumination and detection at which the image was obtained.

Figure 6:
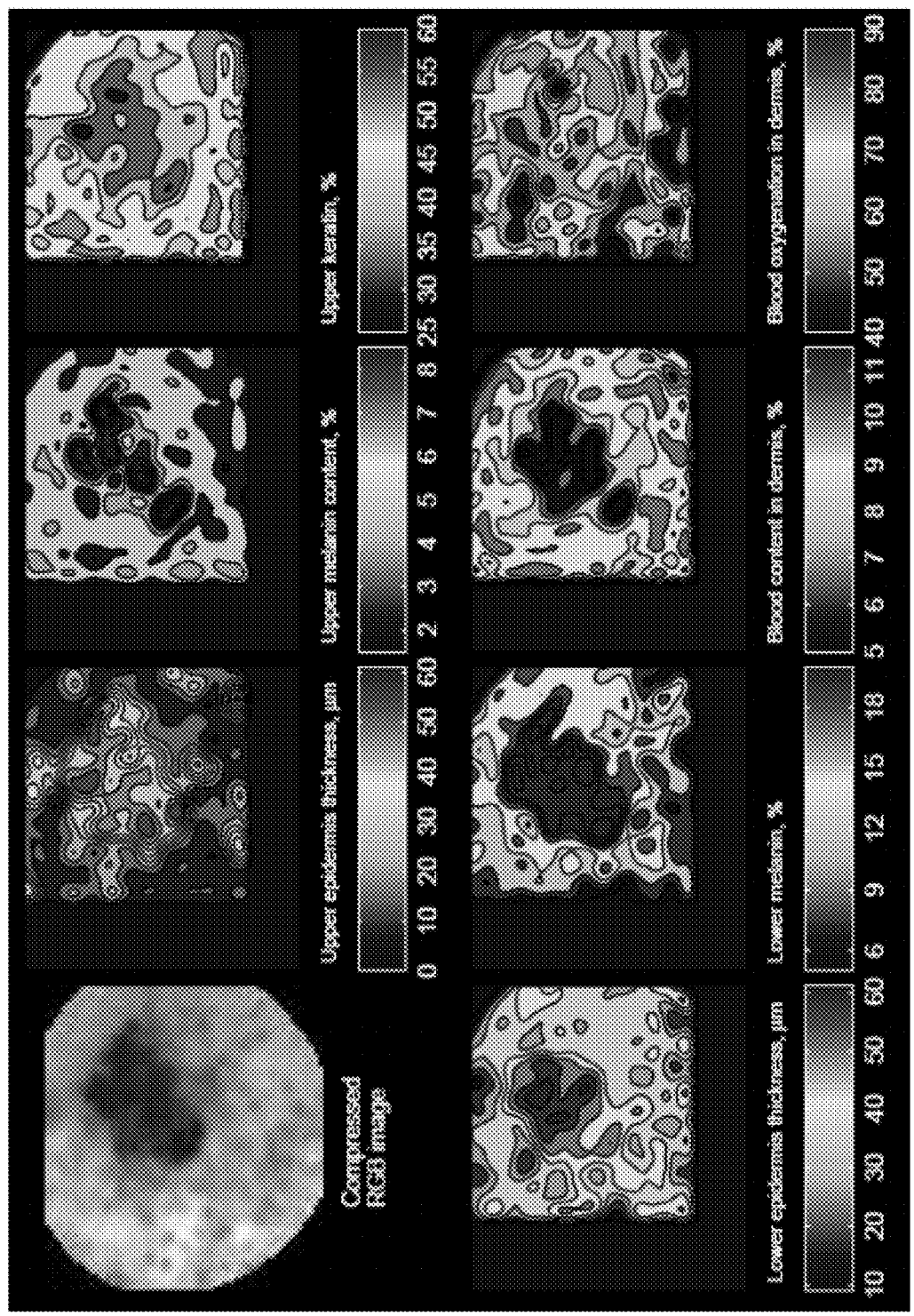
FIG. 6 shows an RGB image and maps of physiology properties and morphological parameters for the melanoma in FIG. 5.
Figure 8:
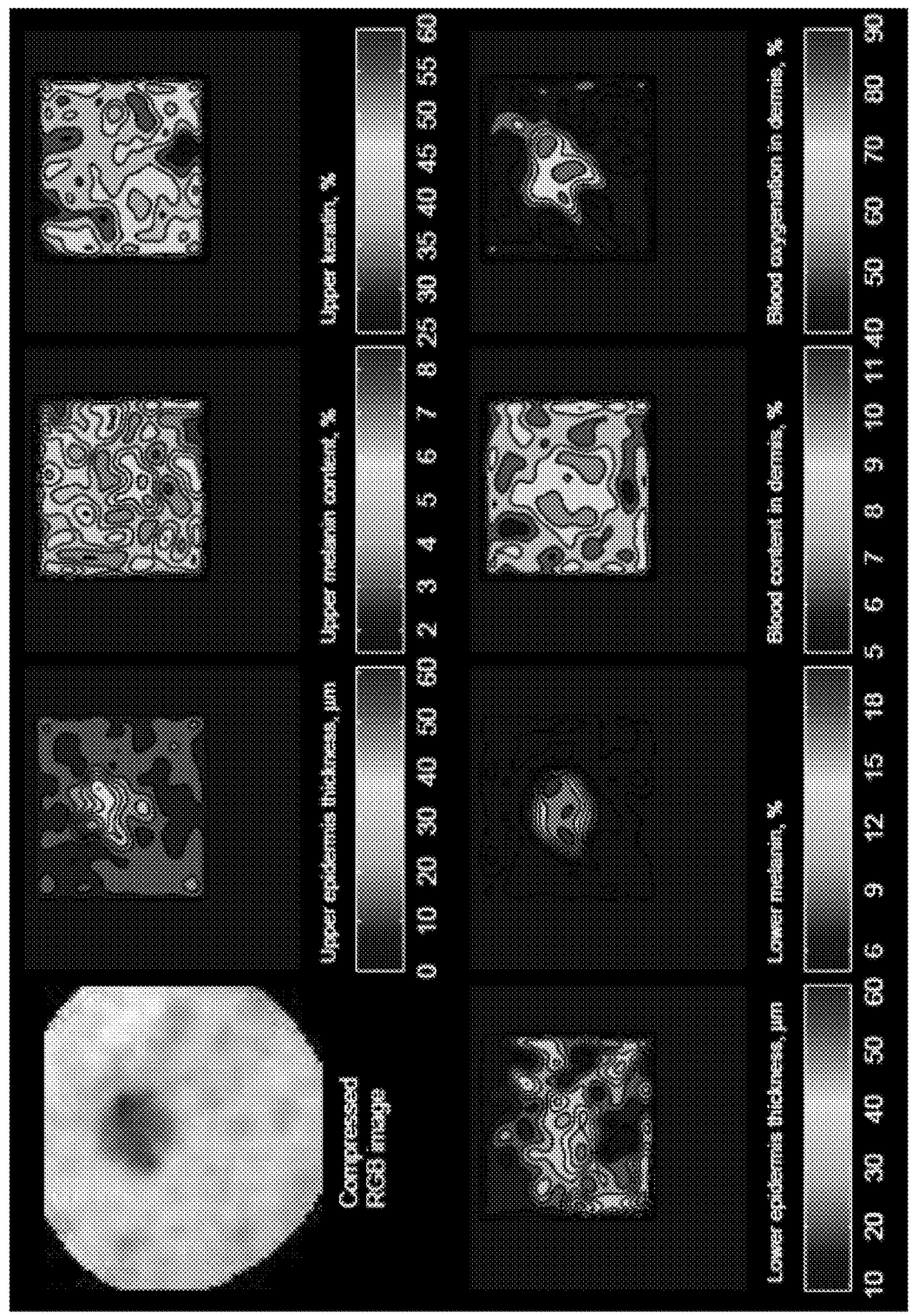
FIG. 8 shows an RGB image and maps of physiology properties and morphological parameters for the compound nevis in FIG. 7.

On the basis of established absorption and transmission spectra for known skin chromophores and mathematical modeling of skin reflectance, a set of recorded images may be used to create maps of physiology properties and morphological parameters of the lesion, which are assumed to be different for benign and malignant tissue. Exemplary maps are shown in FIGS. 6 and 8. The map creation is based on (i) a bio-optical model that relates physiological properties of skin tissue to its inherent optical properties, (ii) a radiative transfer model that for a given set of inherent optical properties computes the light backscattered from the skin for a given wavelength and direction of illumination, and (iii) a nonlinear inversion algorithm that compares the computed backscattered light at various wavelengths and directions with that of the recorded image set.

The data acquisition geometry is designed in such a way that for each combination of illumination and detection directions, the same area of the skin is interrogated. This allows a one-dimensional treatment when the independent-column approximation is invoked and the skin tissue is assumed to have a layered structure: an uppermost layer, the epidermis, consisting of an upper part and a lower part; the dermis, containing the blood circulation; and the subcutis, a strongly scattering fat-containing layer. The inherent optical properties of each layer are the absorption and scattering coefficients as well as the scattering phase function (describing the angular variation of the scattered light), each varying with wavelength. The retrieved physiology properties and morphological parameters are (1) percentage of hemoglobin concentration, (2) percentage of hemoglobin oxygenation, (3) upper epidermal thickness, (4) lower epidermal thickness, (5) percentage of melanosome concentration in upper epidermis, (6) percentage of melanosome concentration in lower epidermis, and (7) percentage of keratin concentration. Each of these seven physiology properties or morphological parameters is retrieved pixel by pixel in the compressed image to create a map covering the zoomed lesion area.

From each map, an entropy value may be calculated and cross entropy values may be calculated for different pairs of maps. The entropy concept used here is similar to that used in statistical physics and information theory. For example, from the spatial distribution of the melanosome concentration, the entropy of this parameter is computed as the melanosome concentration multiplied by its logarithm and integrated over the area of the lesion. These entropy and cross entropy values may be used to define diagnostic parameters, as discussed below.

According to certain embodiments, lesion measurements may comprise a set of 30 images recorded by an OTD scanner. For a given wavelength and direction of illumination, the OTD scanner of the invention records three images simultaneously at different detection angles. This procedure may be repeated for 9 other wavelengths in the range from the near ultraviolet to the near infrared at different illumination angles to produce a lesion measurement that comprises a set of 30 images.

For any of the 30 images, each pixel corresponds to (i) a particular distance from one of the 10 LED sources of different intensity, (ii) a particular size of the of skin area for each of the 20 images that are recorded by one of the two side-viewing cameras; and (iii) a particular location of the illuminated skin area because of possible movement of the skin with respect to the OTD scanner during the few seconds of sequential illumination by the 10 LEDs.

To address issues (i)-(iii) above, a series of pre-processing steps may be performed, including (1) relative calibration such that the intensity of each pixel is measured in units of the intensity due to backscattering for a corresponding pixel from a target having a Lambert surface; (2) geometrical calibration such that an ellipse of illuminated skin area for a side-viewing camera is transformed into a circle; (3) image registration such that each pixel in any of the 30 images corresponds to the same area of the skin; (4) compression such that the raw image having about 7×10⁶ pixels with a spatial resolution of about 25 μm is replaced by a smoothed image with a total number of pixels that is 100 times less than that of the raw image. Thus, the compressed image has 10 times less spatial resolution than the raw image, and a by-product of compression is filtering of spatial high-frequency noise in the raw images due to possible spikes, specular points, and hairs.

Automated zooming may be employed to provide a lesion mask that circumferences the lesion and is characteristic of its shape, and a surrounding mask that creates an area outside the lesion of suitable size and the same outer shape as that of the lesion mask. The zooming can provide rotation, translation, and scaling invariant characteristics of the lesion under investigation, both for calibrated images and maps of physiology properties and morphological parameters. Also, zooming can accelerate the processing since only pixels of the lesion and surrounding masks are considered.

Figure 5:
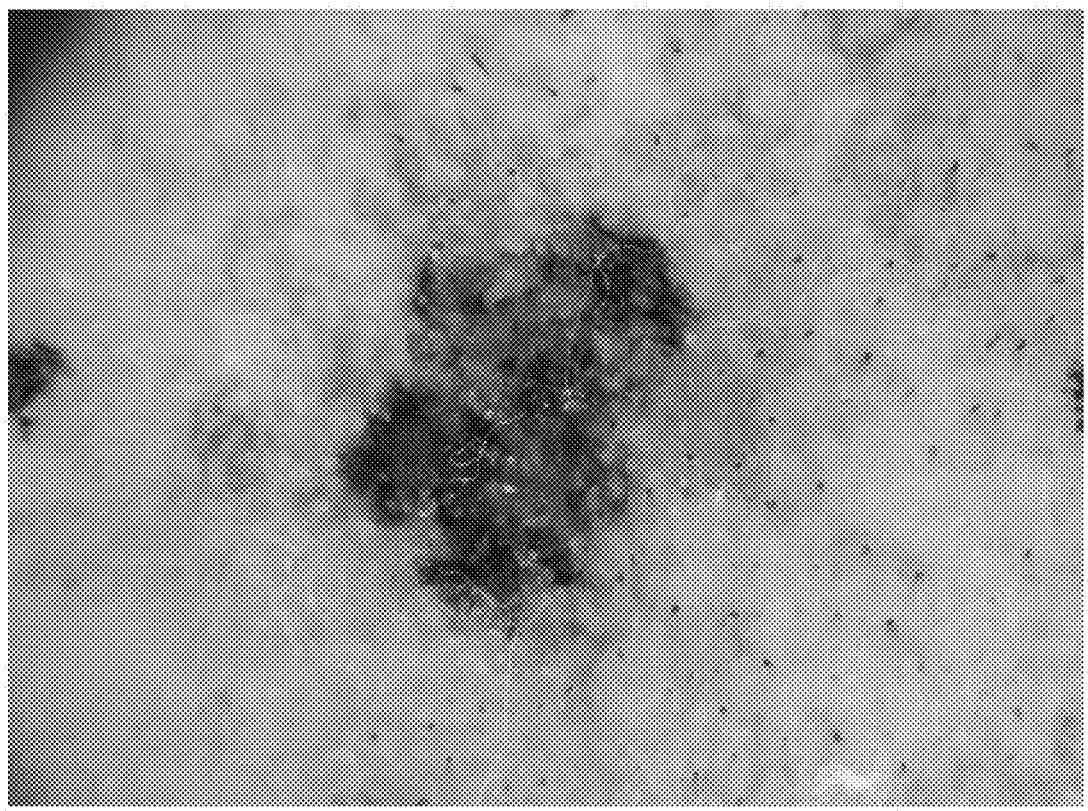
FIG. 5 shows a dermatoscopic image of a melanoma.
Figure 7:
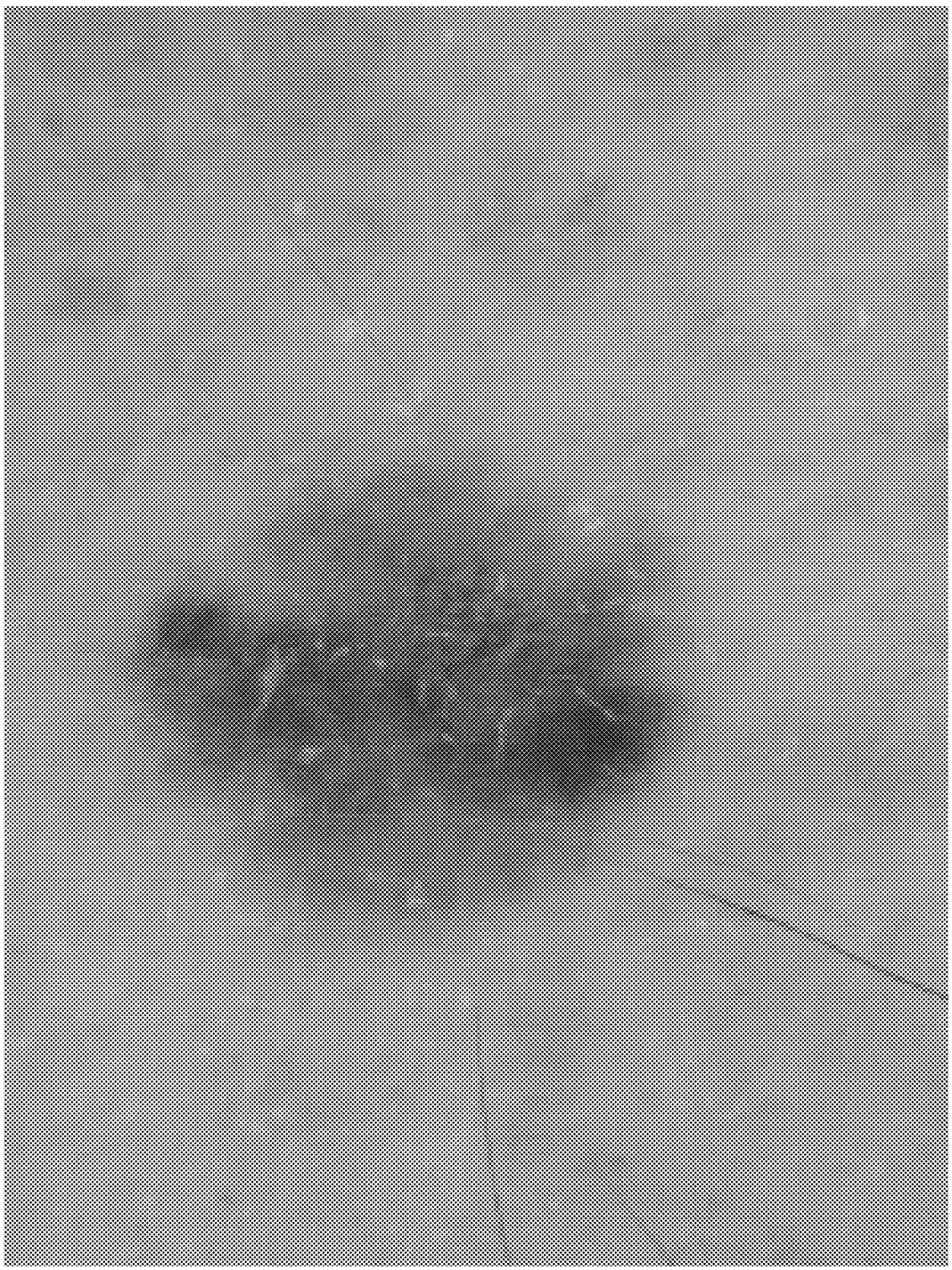
FIG. 7 shows a dermatoscopic image of a compound nevis.

FIG. 5 shows a dermatoscopic image of a melanoma, while FIG. 6 shows the corresponding RGB image and maps of physiology properties and morphological parameters obtained from OTD recordings and processing using systems and methods of the invention. FIGS. 7 and 8 show corresponding results for a compound nevus. Clearly, the maps of physiology properties and morphological parameters in FIG. 6 for a melanoma are quite different from those in FIG. 8 for a compound nevus, indicating that these maps may prove useful in discriminating between benign pigmented lesion and melanomas. As noted above, from these maps, entropy and cross entropy values are calculated and used to define diagnostic parameters, as discussed below.

From the calibrated, registered, compressed, and zoomed OTD image of a lesion obtained from nadir illumination by green light (hereafter referred to as the 'nadir green image') the following 10 morphological parameters may be derived: (1) Size; (2) Histogram width (providing a measure of inhomogeneity of the reflected intensity); (3) Fractal dimension; (4) Moment of inertia; (5) Asphericity; (6) Center distance (representing the physical distance between the geometrical center of the lesion and the center of mass of absorptance); (7) Border length; (8) Average darkness; (9) Area divided by fractal dimension; and (10) Border length divided by fractal dimension.

From the seven maps created from the images, seven entropies and 21 cross entropies are derived, providing a total of 28 physiology properties and morphological parameters. By including also the logarithm of each of the 10 morphological parameters obtained from the nadir green image and the 28 entropy and cross entropy values derived from the seven maps, one obtains a total of 76 diagnostic parameters.

Another 10 diagnostic parameters are derived from the maps of physiology properties:

(1) Maximum value of the melanin optical depth in the lesion area;

(2) Architectural disorder: ratio of maximum to minimum value of the melanin optical depth in the lesion area;

(3) Blood filling: maximum value of blood content in the surrounding area;

(4) Angiogenesis: ratio of the number of blood vessels in a surrounding area close to the lesion border to that in an area farther from the lesion border, given by $C_1A_1L_2=C_2A_2L_1$, where (with j=1, 2) $C_3$ is the blood concentration in area $A_1$, and $L_3$ is the distance from the center of the lesion to the outer border of area $A_3$. Here $A_1$ is a surrounding area close to the lesion border, and $A_2$ is a surrounding area farther from the lesion border;

(5) Ratio of the blood oxygenation in a surrounding area close to the lesion border to that in an area farther from the lesion border, given by $C'_1A_1L_2=C'_2A_2L_1$, where (with j=1, 2) $C'_j$ is the blood oxygenation in area $A_j$, and where $L_3$ and $A_j$ are the same as in the definition above of Angiogenesis;

(6) Melanin contrast: ratio of the total melanin optical depth in the lesion area to that in the surrounding area;

(7) Blood contrast: ratio of the blood content in the lesion area to that in the surrounding area;

(8) High spatial Fourier-components of the map of total melanin optical depth in the lesion area (natural region of interest (RoI), standard gridding);

(9) Entropy of contrast of the map of total melanin optical depth in the lesion area (natural RoI, standard gridding);

(10) The same entropy of contrast as above, but in the original RoI.

Above, natural RoI represents a rectangular area that is oriented in accordance with the shape of the lesion, and "standard gridding" means that along the longest side of the natural RoI there are 100 grid points. The "original RoI" is the rectangular zoom area of the compressed digital image. As discussed above, there are N=86 diagnostic parameters $p_j$ (j=1, 2, ..., N): 2×10 morphological parameters derived from the nadir green image; 2×28 entropies and cross entropies derived from maps of physiology properties and morphological parameters; and 10 additional physiology parameters derived from maps of physiology properties.

For each independent lesion measurement, a diagnostic index D may be defined as a weighted sum of the diagnostic parameters $p_j$:

$$D = w \cdot p. \tag{1}$$

Here the weight vector w consists of N weights $w_j$ (j=1, 2, ..., N), and p is a vector of N diagnostic parameters $p_j$.

Clustering is used to obtain a reliable and robust discrimination between class 1 and class 2 lesions through the identification of a set of class 1 clusters, each comprising a certain number of independent measurements on class 1 lesions, and another set of class 2 clusters, each comprising a certain number of independent measurements on class 2 lesions. A diagnostic indication algorithm can be trained by considering a set of lesions, some belonging to class 1 and others to class 2, for each of which the diagnosis is known, and letting each independent lesion measurement be characterized by N diagnostic parameters $p_j$ (j=1, 2, ..., N). The first step of the clustering procedure is to discretize the diagnostic parameter $p_j$ as follows:

1. Calculate its mean value $\mu_j$ by averaging over the set of independent measurements on class 2 lesions and its standard deviation $\sigma_j$ by averaging over the set of independent measurements on class 1 lesions, which has higher variability than the set of measurements on class 2 lesions.

2. Discretize $p_j$ by setting it equal to $p^*_j$, where $$p^*_j = \begin{cases} -1 & \text{if } p_j < \mu_j - 0.7\sigma_j \\ 0 & \text{if } \mu_j - 0.7\sigma_j < p_j < \mu_j + 0.7\sigma_j \\ +1 & \text{if } p_j > \mu_j + 0.7\sigma_j \end{cases} \tag{2}$$

where the cutoff value of $\sigma_j$ is chosen in order to ensure a fair representation of the set of measurements on class 2 lesions. Thus, each discretized diagnostic parameter $p^*_j$ has a value different from zero only if the value of $p^*_j$ is sufficiently far away from the mean value $\mu_j$.

The definition of a clustering index for an independent lesion measurement is based on constructing coincidence vectors $C^+$ and $C^-$ and probabilistic vectors $t^+$ and $t^-$:

$$C^\pm = \{T_1^\pm, T_2^\pm, \ldots, T_N^\pm\}; \quad t^\pm = \{t_1^\pm, t_2^\pm, \ldots, t_N^\pm\} \quad (3)$$

where the components $T_j^\pm$ are coincidence parameters given by $T_j^+=1$ if $p^*_j=+1$ and $T_j^+=0$ otherwise; $T_j^-=1$ if $p^*_j=-1$ and $T_j^-=0$ otherwise; and where $t_j^\pm = (\Sigma T_j^\pm)^{1/2}$, the sum being over all independent measurements on lesions of the class under consideration. Thus, each component $t_j^+$ (or $t_j^-$) (j=1, 2, ..., N) is the square root of an integer that is equal to the total number of times $p^*_j$ has the value +1 (or −1) among all independent measurements on lesions of the class under consideration.

The clustering index C for an independent measurement on either a class 1 or a class 2 lesion is given by:

$$C = t^+ \cdot C^+ + t^- \cdot C^-. \quad (4)$$

The independent measurements are ordered in accordance with the value of the clustering index, and independent measurements having values of the clustering index in a specific interval are taken to belong to the same cluster.

To construct clusters of independent measurements on class 1 lesions relative to the entire set of independent measurements on class 2 lesions, the class 1 measurement having the highest clustering index is taken, as given by Eq. (4). Then $c_m$ independent measurements are added to this one to obtain a total of $c_{m+1}$ independent measurements in this first cluster, where $c_m$ is obtained from the requirement that the function F(c), given by $$F(c) = S(c) \times \tanh\left(10\frac{c+1}{C}\right) \quad (5)$$

shall have its maximum value when $c=c_m$. Here C is the total number of independent measurements belonging to the available set of independent measurements on class 1 lesions, and S(c) is the specificity, i.e. the ratio between the number of correctly classified independent measurements on class 2 lesions and the total number of independent measurements on class 2 lesions. The second factor on the right-hand side of Eq. (5), which increases monotonically with c, linearly for small values and then more slowly, allows for inclusion of many independent measurements in a cluster, but its influence gets weaker as the number c increases, making the specificity decisive.

The number $c_m$ of ordered independent measurements on class 1 lesions relative to the entire set of independent measurements on class 2 lesions may then found such that the corresponding cluster provides a maximum value of the function F(c) in Eq. (5) for $c=c_m$. Here ordered implies that the independent measurements are placed in sequential order in accordance with the value of the clustering index. Let us define a virtual cluster as a cluster with a number c of ordered independent measurements on class 1 lesions relative to the entire set of independent measurements on class 2 lesions, whereas the corresponding actual cluster contains the optimum number $c=c_m$ of ordered independent measurements on class 1 lesions relative to the entire set of independent measurements on class 2 lesions. The details of an exemplary cluster construction procedure is as follows:

1. Consider a virtual cluster defined by the number c relative to the entire set of independent measurements on class 2 lesions. Start by letting c=1, then add one ordered independent measurement on class 1 lesions, so that c becomes equal to 2, and apply the procedure described in items 2-5 below.

2. Minimize the cost function in Eq. (14) to obtain an optimal generalized weight vector e that gives a diagnostic index value D, as defined in Eq. (15), for an independent measurement on a lesion belonging to either class 1 or class 2.

3. Calculate the diagnostic index values (D values) (i) for all ordered independent measurements on class 1 lesions in the given virtual cluster and (ii) for all independent measurements on class 2 lesions.

4. Choose a threshold for the D values (after the calculation of D values in item 3 above) to obtain a binary classification rule, according to which an independent measurement having a D value that is larger (smaller) than the threshold value corresponds to a class 1 (class 2) lesion. Thus, all independent measurements belonging to class 1 have D values larger than the threshold value, implying 100% of correctly classified independent measurements on class 1 lesions (i.e. sensitivity of 100%).

5. For the chosen threshold, calculate the specificity S(c) in Eq. (5), which is the number of correctly classified independent measurements on class 2 lesions (having D values smaller than the threshold) divided by the total number of independent measurements on class 2 lesions in the training ensemble. Check whether F(c) in Eq. (5) increased due to the addition of one ordered independent measurement on class 1 lesions. If it did not increase, let the current value of c be equal to $c_m$. Otherwise, increase the number c by 1 and return to item 2 above 6. Typically, three independent measurements are performed on each lesion, and if two of the three independent measurements are found to belong to the same cluster, then the third independent measurement is also taken to belong to that cluster. If only one of three independent measurements on a lesion is found to belong to a cluster, the lesion is not included in that cluster, but left for further consideration in the clustering process.

7. Construct the next cluster belonging to the remaining set of measurements on class 1 lesions relative to the entire set of measurements on class 2 lesions in a similar manner, starting with the measurement having the highest clustering index among the lesion measurements not included in the previous cluster.

Suppose a total of $L_1$ clusters is constructed of independent measurements on class 1 lesions relative to the entire set of independent measurements on class 2 lesions. Similarly to what was done in the construction of clusters of independent measurements on class 1 lesions, the independent measurement on class 2 lesions having the highest clustering index are taken, as defined in Eq. (4), and $c_m$ independent measurements are added to this independent measurement to obtain a total of $c_m+1$ measurements in this first cluster among class 2 lesions, where $c_m$ is obtained from the requirement that the function F(c), given by Eq. (5), shall have its maximum value when $c=c_m$. Here C is the total number of measurements belonging to the available set of independent measurements on class 2 lesions, and S(c) is the sum of specificities for the cluster under construction vs. each of the clusters of class 1 lesions. The specificity S(c) for the cluster under construction vs. cluster #i of class 1 lesions is the ratio between the number of correctly classified measurements of class 2 lesions and the total number of measurements on class 2 lesions contained in the cluster under construction. Thus, S(c) is given by $$S(c) = \sum_{i=1}^{L_1} S_i(c). \tag{6}$$

The clustering procedure can then be carried out similarly to the procedure enumerated above for class 1 lesions relative to the entire set of class 2 lesions.

Optimal values of the weights in Eq. (1) are then determined for separation between the two classes of lesions, called class 1 and class 2. The dimension of the optimization problem is reduced by (i) introducing a covariance matrix for independent measurements on lesions of class 1 and class 2, where the two classes are chosen such that the trace of the covariance matrix for class 1 lesions is larger than that for class 2 lesions, (ii) defining a discriminating operator in terms of the two covariance matrices, (iii) constructing eigenvectors and eigenvalues on the basis of the discriminating operator and using only those eigenvalues that are larger than a threshold value, chosen so as to ensure that sufficiently large variations of the diagnostic parameters associated with independent measurements on class 1 lesions are accounted for, and (iv) defining for each independent measurement on a lesion of class 1 or class 2 a set of generalized diagnostic parameters. As a result, Eq. (1) becomes $$D = \tilde{w} \cdot \tilde{p} \tag{7}$$

where $\tilde{w}$ and $\tilde{p}$ are generalized weight and diagnostic parameter vectors, respectively, each having a dimension $\tilde{N}$ that is typically only one third of the number N of original diagnostic parameters.

In order to reduce the dimension of the optimization problem, a set of generalized diagnostic parameters is defined by introducing a covariance matrix for each of the two classes of lesions, given by $$\hat{V}^{(1)} = \frac{1}{M_1 - 1} \sum_{i=1}^{M_1} (p_i^{(1)} - \langle p^{(1)} \rangle)(p_i^{(1)} - \langle p^{(1)} \rangle)^T \tag{8}$$

$$\hat{V}^{(2)} = \frac{1}{M_2 - 1} \sum_{i=1}^{M_2} (p_i^{(2)} - \langle p^{(2)} \rangle)(p_i^{(2)} - \langle p^{(2)} \rangle)^T \tag{9}$$

where the superscript T denotes the transpose, $p_i^{(q)} = \{p_{i,1}^{(q)}, p_{i,2}^{(q)}, \ldots, p_{i,N}^{(q)}\}$ (q=1,2) is the vector of diagnostic parameters comprised of N components for independent measurement #i on lesions belonging to class q=1 or q=2, $\langle p^{(q)} \rangle$ is the average value of the diagnostic vectors for all independent measurements on lesions belonging to class q, and $M_q$ is the number of independent measurements on lesions belonging to class q. Note that by definition, independent measurements on lesions belonging to class 1 have a larger value of the trace of the covariance matrix than those belonging to class 2, i.e. $\mathrm{Tr}\{\hat{V}^{(1)}\} > \mathrm{Tr}\{\hat{V}^{(2)}\}$. The next step is to introduce a discriminating operator, defined by $$\hat{D} = [\hat{V}^{(2)}]^{-1/2} [\hat{V}^{(1)}] [\hat{V}^{(2)}]^{-1/2} \tag{10}$$

which is a generalization of the signal-to-noise ratio for multivariate random signals. To discriminate between independent measurements on lesions belonging to class 1 and class 2 and reduce the dimension of the optimization problem we extract eigenvectors $d_\alpha$ according to $$\hat{D} d_\alpha = \alpha d_\alpha \tag{11}$$

and introduce a subset of eigenvectors $d_{\alpha k}$ for each of which the eigenvalue $\alpha_k > \alpha_{min}$, where $\alpha_{min}$ is chosen to be equal to or larger than 0.7 in order to ensure that one accounts for sufficiently large variations of the diagnostic parameters associated with independent measurements on class 1 lesions.

For an independent measurement on a lesion of class 1 or class 2, we define a vector $\tilde{p}$ of generalized diagnostic parameters:

$$\tilde{p} = \{d_{\alpha 1} \cdot \Delta p, d_{\alpha 2} \cdot \Delta p, \ldots, d_{\alpha min} \cdot \Delta p\}. \tag{12}$$

Here $\Delta p = p - \langle p^{(2)} \rangle$ where p is the vector of original diagnostic parameters in Eq. (1) and $\langle p^{(2)} \rangle$ is the average of the vectors of diagnostic parameters for all independent measurements on class 2 lesions.

The condition $\alpha_k > \alpha_{min}$ leads to a substantial reduction in the number of diagnostic parameters. Thus, the number $\tilde{N}$ of generalized diagnostic parameters is typically only one third of the number N=86 of original diagnostic parameters. The generalized diagnostic index for an independent measurement on a lesion of class 1 or class 2 is given by:

$$D = \tilde{w} \cdot \tilde{p} \tag{13}$$

where $\tilde{w}$ has the same dimension as $\tilde{p}$.

To determine optimal values of the weights in Eq. (5) a cost function is defined, consisting of a master term and a constraint term, where the latter is used to constrain the length of the weight vector to lie on the surface of a hypersphere in $\tilde{N}$ dimensions of radius equal to 1. For discussion of the master term of the cost function, consider a set of independent lesion measurements that is divided into one subset of independent measurements on lesions belonging to class 1 and another subset of independent measurements on lesions belonging to class 2. As an example, class 1 could comprise independent measurements on malignant lesions and class 2 independent measurements on benign lesions.

For each generalized weight vector $\tilde{w}$, the corresponding generalized diagnostic index $D_1(\tilde{w})$ is computed for each of the class 1 independent lesion measurements as well as the corresponding generalized diagnostic index $D_2(\tilde{w})$ for each of the class 2 independent lesion measurements. Next, the mean values $\langle D_1 \rangle$ and $\langle D_2 \rangle$ and the corresponding standard deviations $\sigma_1$ and $\sigma_2$ are computed. The master term of the cost function is given in terms of these parameters as $$J_0(\tilde{w}) = \frac{1}{\sigma_1} \int_{D^*(\tilde{w})}^{\infty} \exp\left\{-\frac{[D - \langle D_1 \rangle]^2}{2\sigma_1^2}\right\} dD + \frac{1}{\sigma_2} \int_{-\infty}^{D^*(\tilde{w})} \exp\left\{-\frac{[D - \langle D_2 \rangle]^2}{2\sigma_2^2}\right\} dD \tag{14}$$

where $D^*(\tilde{w})$ is the point of intersection of the two Gaussian distributions in Eq. (14), and the value of $J_0(\tilde{w})$ is the area of overlap of the two Gaussian distributions. The minimization of $J_0(\tilde{w})$ will provide the smallest degree of overlap between the two Gaussian distributions, and hence the best separation between independent measurements on class 1 and class 2 lesions. After minimization of the cost function, Eq. (7) becomes $$D = e \cdot \tilde{p} \tag{15}$$

where e is an optimal generalized weight vector, hereafter referred as an expert regarding the separation between independent measurements belonging to the two classes of lesions.

For a pair of opposite clusters, consisting of cluster #i of class 1 lesions and cluster #j of class 2 lesions, a probabilistic characterization of an expert can be obtained by proceeding as follows:

1. For each independent lesion measurement included in a pair of opposite clusters, the D value is computed, given by Eq. (15), where e is the expert.

2. Two histograms may be constructed, one for each of the clusters in the pair, where each histogram represents the number of independent measurements having D values within different bins in the interval between the minimum D value ($D_{min}$) and the maximum D value ($D_{max}$).

Figure 9:
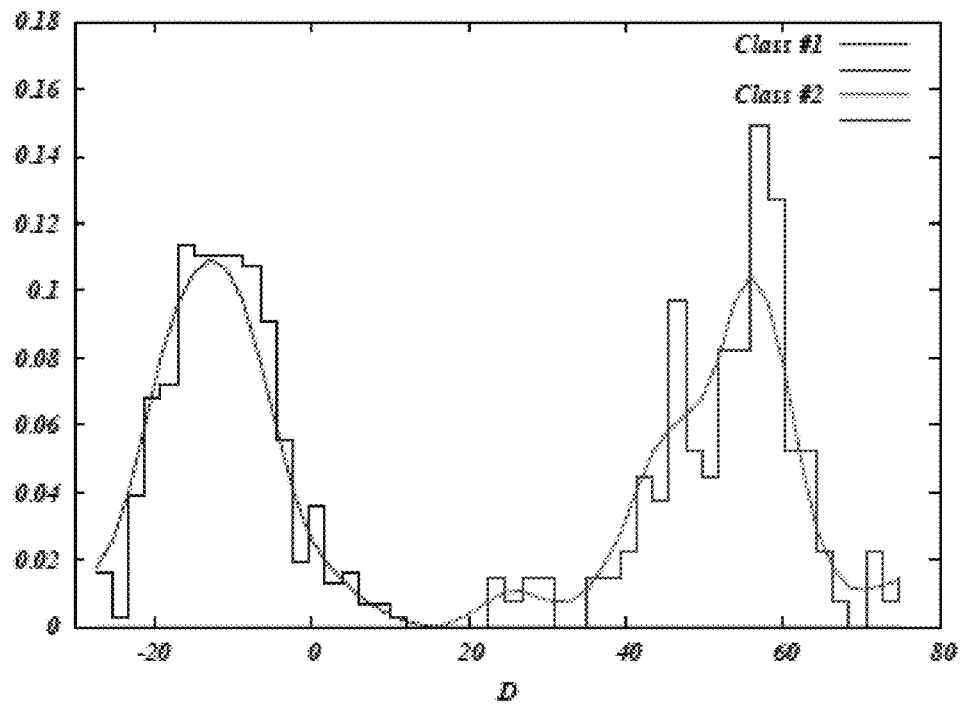
FIG. 9 shows histograms of two classes of lesions and corresponding smooth representations.

Here $D_{min}$ is the absolute value of the largest negative D value for class 2 lesions (see blue curve in FIG. 9), and $D_{max}$ is the largest D value for class 1 lesions (see red curve in FIG. 9). As a result, the two histograms are obtained (red for class 1 and blue for class 2) as illustrated by the vertical lines in FIG. 9.

3. Next, the corresponding two smooth histograms shown in FIG. 9 are constructed that represent probability density functions (pdfs).

4. Finally, the blue (class 2) pdf in FIG. 9 is integrated from $D_{min}$ to a given D value and the red (class 1) pdf from a given D value to $D_{max}$ to obtain the corresponding cumulative distributions in FIG. 10.

Figure 10:
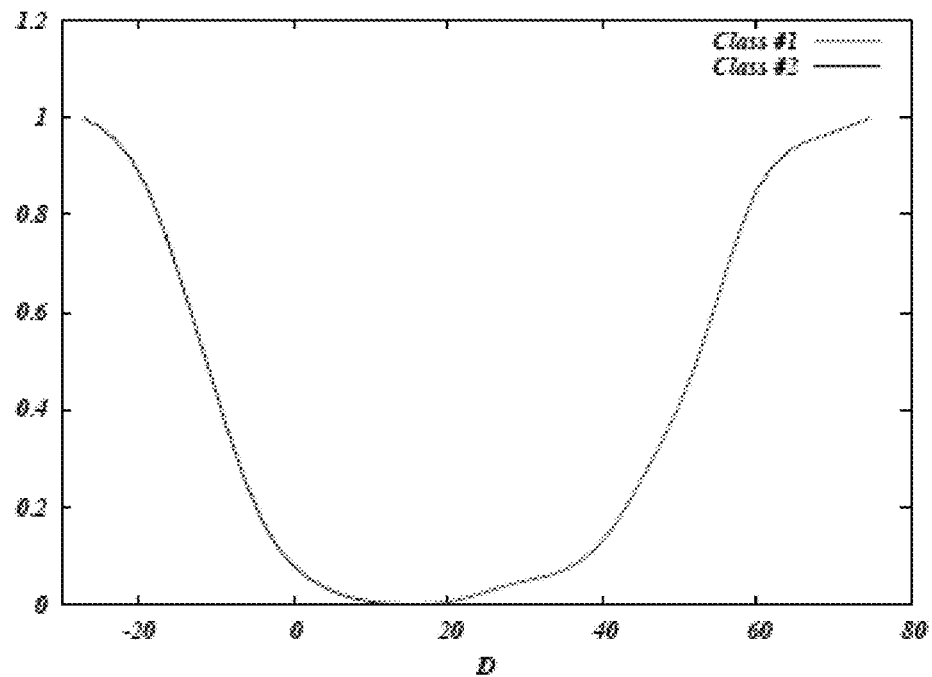
FIG. 10 shows cumulative distributions corresponding to the smooth histograms of FIG. 9.

For an independent lesion measurement having a certain D value, the corresponding points on the two distribution curves in FIG. 10 may be interpreted as partial reliabilities of a diagnostic indication.

If $r_{i,j}^{(1)}(D)$ represents the red (class 1) curve in FIG. 10 and $r_{i,j}^{(2)}(D)$, represents the blue (class 2) curve, then, by definition, $r_{ij}^{(1)}(D)[r_{ij}^{(2)}(D)]$ represents the partial reliability of a diagnostic indication in favor of the measurement belonging to a class 1 [class 2] lesion.

The number of class 1 and class 2 clusters may be represented by $L_1$ and $L_2$, respectively, and a modified diagnostic index $\tilde{D}$ can be defined by $$\tilde{D} = \text{sign}(\delta_i) |\delta_i|_{max}^{1/L} \quad (16)$$

where $L = L_1 \times L_2$ and $$\delta_i = \prod_{j=1}^{L_2}(r_{i,j}^{(1)} + \epsilon) - \prod_{j=1}^{L_2}(r_{i,j}^{(2)} + \epsilon) \quad (17)$$

with $|\delta_i|_{max}$ being the largest of the $|\delta_i|$ values for $i=1, 2, \ldots, L_1$. The value $\epsilon=0.001$ is used to avoid zeros appearing in the products in Eq. (17).

The diagnostic indication by a team of experts associated with a randomly drawn training ensemble comprised of L1 and L2 clusters of class 1 and class 2, respectively, is that if $\tilde{D}$ given by Eq. (16) is greater than or equal to zero, then the measurement is regarded to represent a class 1 lesion. Typically three measurements are taken of each lesion, and the diagnostic indication for a lesion by a team of experts associated with this randomly drawn training ensemble is that if the mean value of the modified diagnostic indices $\tilde{D}$ given by Eq. (16) for the measurements taken is greater than or equal to zero, the lesion is regarded to be of class 1. This diagnostic indication constitutes a nonlinear binary classifier.

In order to construct a final diagnostic indication tool, a large number of different training and validation ensembles may be drawn at random (for example, K=144 such ensembles, see FIGS. 11 and 12) by proceeding as follows:

1. Drawing at random a major part (e.g. 77%) of the independent measurements on lesions belonging to each of class 1 and class 2 and let them constitute a training ensemble, and let the remaining independent lesion measurements constitute a validation ensemble. All multiple measurements on any lesion are included into either the training or the validation ensemble.

2. The above procedure is repeated K=144 times to obtain K different training and validation ensembles, where each randomly drawn training ensemble consists of a major part (e.g. 77%) of the independent measurements on lesions belonging to each of class 1 and class 2, and where the corresponding validation ensemble consists of the remaining independent lesion measurements.

3. Constructing statistically independent experts by (a) using the set of all experts $e_{j(i)}$ arising from K randomly drawn training ensembles, where $j(i)=1, 2, \ldots, J(i)$, $i=1, 2, \ldots, K$ (with J(i) being the number of experts associated with randomly drawn training ensemble #i) and the corresponding derivatives $d_{rj(i)}^{(1)}/dD$ of the partial reliabilities to compute a matrix S representing the moment of inertia for the set of lesion measurements of class 1, given by $$S = \sum_{i=1}^{K}\sum_{j=1}^{J(i)}\left[e_{j(i)}\int_0^{D_{max}}(dr_{j(i)}^{(1)}/dD)dD\right]\left[e_{j(i)}^T\int_0^{D_{max}}(dr_{j(i)}^{(1)}/dD)dD\right]; \quad (18)$$

(b) finding the principal components $s_\lambda$ ($\lambda=1, 2, \ldots, L^*$) of S; and (c) selecting, for each value of $\lambda$, those three experts that have the largest values of the scalar product $e_{j(i)}*s_\lambda$ to obtain $3 \times L^*$ candidate experts, and hence $3^{L^*}$ possible combinations of experts for the final diagnostic indication tool.

The best combination of experts for the final diagnostic indication tool can be obtained by constructing the matrices $\Sigma_{\lambda=1}^{L^*} e_{k',\lambda} \lambda e_{k',\lambda'}^T$, where $e_{k',\lambda}$ represents one of the $3^{L^*}$ possible combinations of experts, and choosing that particular combination $e_{k',\lambda}$ of $L^*$ experts among the $3^{L^*}$ possible combinations, which gives the $L^*$ largest values for the determinant of these matrices. A typical number of principal components or "best" experts is $L^*=12$.

The final diagnostic indication tool described above may be applied to an unknown lesion measurement as follows:

1. For each of the $L^*$ "best" experts of the final diagnostic indication tool, the diagnostic index is calculated for the unknown lesion measurement, and the corresponding reliability values for class 1 and class 2 are found.

2. If the sum of the four largest values of the difference between the reliability for class 1 and that for class 2 is greater than zero, the indication is regarded to be that of a class 1 lesion.

In order to increase the robustness of the maps of physiology properties and morphology parameters obtained by the OTD inversion procedure, statistical information extracted from multiple measurements (typically three) of each lesion may be employed. After compression, each of the 30 images comprising a lesion measurement consists of approximately 10,000 pixels. For each of the 10 different wavelengths $\lambda_i$ (i=1, 2, \ldots, 10), the average value $I_{\lambda,i,m}$ may be computed for measurement #m of the reflected light for each pixel inside the area surrounding the lesion:

$$I_{\lambda_i,m} = \frac{1}{N_p}\sum_{n=1}^{N_p} I_{\lambda_i,m,n} \quad (i = 1, 2, \ldots, 10) \quad (19)$$

where $I_{\lambda_i,m,n}$ is the reflected light for pixel #n and measurement #m, and $N_p$ is the total number of pixels inside the area surrounding the lesion. Next, several measurements of the same lesion are averaged:

$$I_{\lambda_i} = \frac{1}{M}\sum_{m=1}^{M} I_{\lambda_i,m} \quad (i = 1, 2, \ldots, 10) \quad (20)$$

where M is the number of measurements (typically 3). Then column vectors are defined $$I_m = [I_{\lambda_1,m}, I_{\lambda_2,m}, \ldots, I_{\lambda_{10},m}]^T \quad (21)$$

$$I = [I_{\lambda_1}, I_{\lambda_2}, \ldots, \ldots, I_{\lambda_{10}}]^T \quad (22)$$

where T denotes the transpose. A difference vector is defined $$\Delta I_m = I_m - I \quad (23)$$

and the covariance matrix $\hat{C}_l$ for lesion #l: is estimated as follows:

$$\hat{C}_l = \frac{1}{M-1}\sum_{m=1}^{M} \Delta I_m [\Delta I_m]^T \quad (24)$$

which is a 30×30 matrix. All available lesions (l=1, 2, ..., L) are averaged to obtain $$\hat{C} = \frac{1}{L}\sum_{l=1}^{L} \hat{C}_l \quad (25)$$

which represents the uncertainties in the measurements.

An estimate of the misfit between measured and simulated reflected light for a given pixel (after compression) is given by:

$$\mathcal{J}_0 = [i_{\lambda_i,n} - \hat{i}_{\lambda_i,n}]^T [\hat{C}]^{-1} [i_{\lambda_i,n} - \hat{i}_{\lambda_i,n}] \quad (26)$$

(See Nielsen, et al., "Retrieval of the physiological state of human skin from UV-Vis reflectance spectra: A feasibility study," Photochem. Photobiol. B 93, 23-31 (2008), incorporated herein by reference).

where $i_{\lambda_i,n}$ is the measured reflected light for pixel #n and wavelength $\lambda_i$, and $\hat{i}_{\lambda_i,n}$ is the simulated reflected light for pixel #n and wavelength $\lambda_i$.

Use of the result in Eq. (26) in the inversion procedure makes the resulting maps of physiology properties and morphological parameters more robust. Thus, the difference between maps obtained from different measurements of the same lesion becomes significantly smaller. This modification of the inversion procedure requires that it is possible to identify the same area (in the present case the surrounding area of the lesion, which is much brighter than the lesion area) in images corresponding to different measurements of the same lesion and also in images corresponding to different wavelengths $\lambda_i$. It can be shown that the reduced variance of integrated parameters, such as the entropies, will result in increased robustness in the sense of reduced variance of the diagnostic parameters $p_{ij}$ (i=1, 2, . . . , N) among multiple measurements on the same lesion #i.

Example 1

The classification scheme was developed and optimized on a clinical data set consisting of 1,495 lesion images collected in several clinical studies using OTD devices from 2005 to date. A final diagnostic indication tool was constructed based on K=144 different diagnostic indication rules, each designed to discriminate between suspicious and benign lesions in a population of unselected ("all-comer") lesions. For training of any of these K diagnostic indication rules 77% of all available measurements performed on a total of 712 lesions (including 80 malignant lesions) were drawn at random, while the remaining 23% of the measurements were used for validation. Typically three measurements were performed on each lesion. For the 712 lesions used for training and validation, the histopathological diagnoses for the dermatoscopically suspicious lesions as well as the diagnoses for the dermatoscopically benign lesions are given in Table 1.

TABLE 1

| Type of lesion | No. of lesions |
|---|---|
| Melanoma (n = 64) | |
| in situ | 21 |
| invasive | 43 |
| Basal cell carcinoma (n = 13) | |
| pigmented basal cell carcinoma | 5 |
| reticulated basal cell carcinoma | 1 |
| superficial basal cell carcinoma | 3 |
| nodular basal cell carcinoma | 4 |
| Squamous cell carcinoma (n = 3) | |
| in situ | 2 |
| invasive | 1 |
| Nevus (n = 604) | |
| ordinary compound | 551 |
| inflamed compound | 3 |
| irritated compound | 3 |
| congenital compound | 1 |
| lentiginous compound | 1 |
| traumatized compound | 1 |
| mildly dysplastic melanocytic | 1 |
| spitz | 1 |
| ordinary junctional | 28 |
| lentiginous junctional | 2 |
| dermal | 9 |
| intradermal | 3 |
| Keratosis (n = 28) | |
| porokeratosis | 2 |
| pigmented actinic keratosis | 9 |
| pigmented seborrheic keratosis | 15 |
| lichenoid actinic keratosis | 2 |

Clusters of lesions are constructed for each of the two classes of lesions, between which discrimination is desired, say $L_1$ and $L_2$ clusters of class 1 and class 2, respectively. Each of the randomly drawn K=144 training and validation ensembles gives its own diagnostic indication rule, so in total there will be 144 different diagnostic indication rules, and for each of them there will be $L_1 \times L_2$ different experts (nonlinear binary classifiers), each between a pair of opposite clusters. Thus, in total there will be about $L_1 \times L_2 \times 144$ different experts. Typically, there will be 5 or 6 clusters of each class. As an example, if there were $L_1 = 6$ clusters of class 1 and $L_2 = 5$ of class 2, the total number of experts would be 4,320, among which, only the L* "best" experts would be used for construction of the final diagnostic indication tool.

The accuracy A of a binary classifier is a measure of how correctly it can identify elements belonging to each of two classes, i.e.

$$A = \frac{\text{number of correct assessments}}{\text{number of all assessments}}. \tag{27}$$

Alternatively, the accuracy can be expressed in terms of the sensitivity and specificity and the occurrence rates of the elements belonging to the two classes. If the occurrence rate is $N_1$ for class 1 and $N_2$ for class 2, and a binary classifier has sensitivity Se and specificity Sp, a measure of the accuracy is given by $$A = \frac{N_1 Se + N_2 Sp}{N_1 + N_2}. \tag{28}$$

Figure 11:
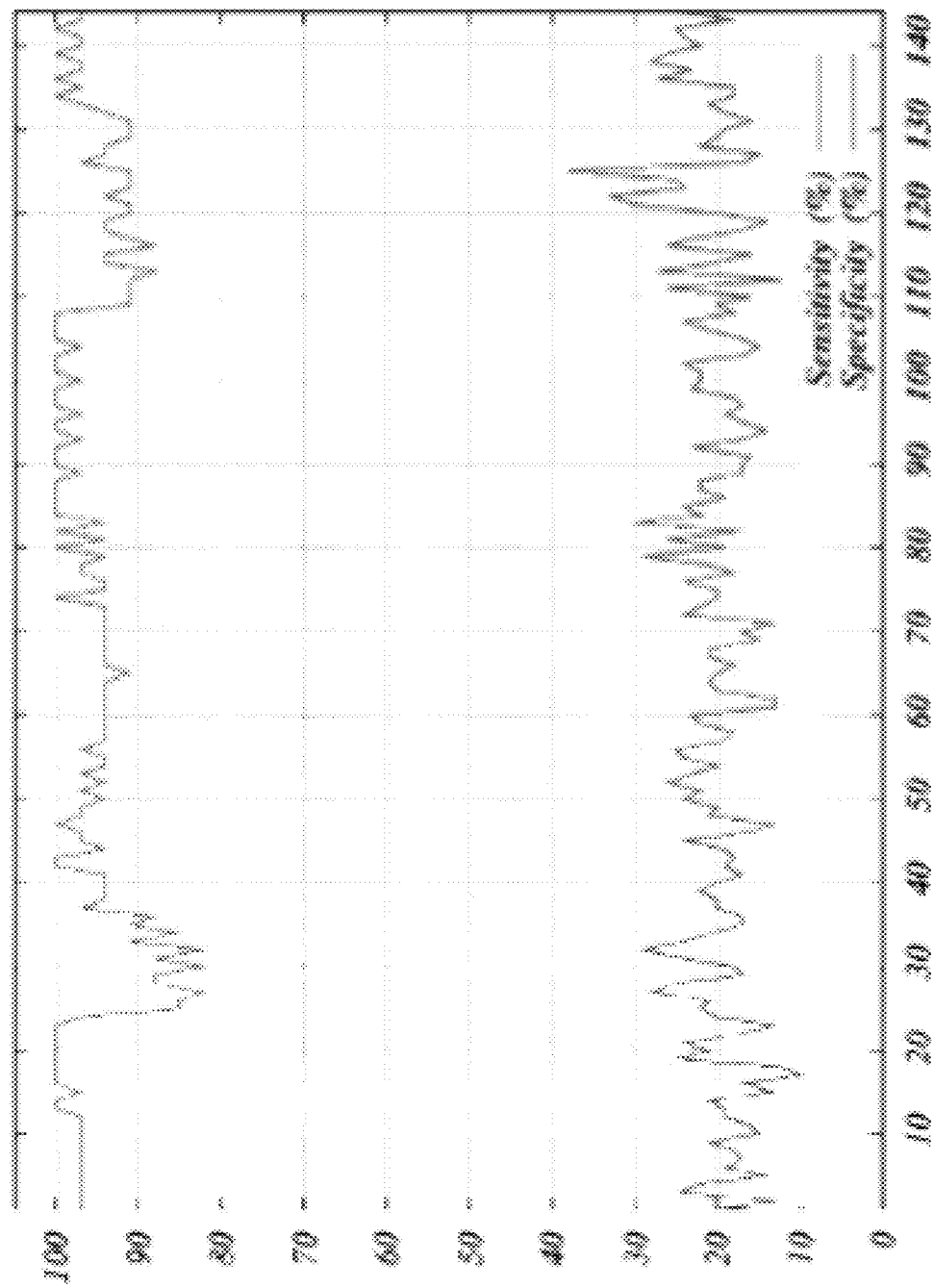
FIG. 11 shows sensitivity (red) and specificity (blue) for 144 different randomly drawn training and validation sets each consisting of 137 lesions considered to be suspicious.

FIG. 11 shows the performance in terms of sensitivity and specificity of our binary classifiers for discriminating between malignant and benign lesions for 144 different, randomly drawn training and validation ensembles. In each of the 144 cases included in FIG. 12, the data set consisted of 34 malignant lesions and 103 benign lesions, all taken from a set of lesions considered by experienced dermatologists to be suspicious and therefore biopsied. In each case, the classifier was trained using 77% of the available data, chosen at random, while the remaining 23% of the data not used for training constituted a validation set. From FIG. 12, the sensitivity and specificity are estimated to be 0.95 and 0.20, respectively, so that Eq. (28) gives $$A = \frac{34 \times 0.20 + 103 \times 0.95}{34 + 103} = 0.39. \tag{29}$$

In the US, around 2.5-3 million skin lesions are biopsied annually and a fraction of these—between 50,000 and 100,000—are diagnosed as melanoma, implying that according to Eq. (11), the accuracy is less than 0.04:

$$A < \frac{100,000}{2,500,000} = 0.04. \tag{30}$$

In comparison, the present binary classifiers for a similar sampling of lesions would give an accuracy, according to Eq. (28), of $$A = \frac{100,000 \times 0.95 + (2,500,000 - 100,000) \times 0.20}{2,500,000} = 0.23 \tag{31}$$

in spite of no access to medical case histories, which are generally available to dermatologists. Note also that the final diagnostic indication tool above, which is based on the 12 "best" experts among the 144 binary classifiers for randomly chosen training and validation sets, gave a sensitivity higher than 0.98 for a specificity of 0.36 when applied to a set of clinically suspicious lesions.

This result implies that the final diagnostic indication tool can serve as a well-qualified expert, acting in a fast automatic mode to help dermatologists arrive at the correct decision for complicated cases, and thus help eliminate unnecessary biopsies.

Figure 12:
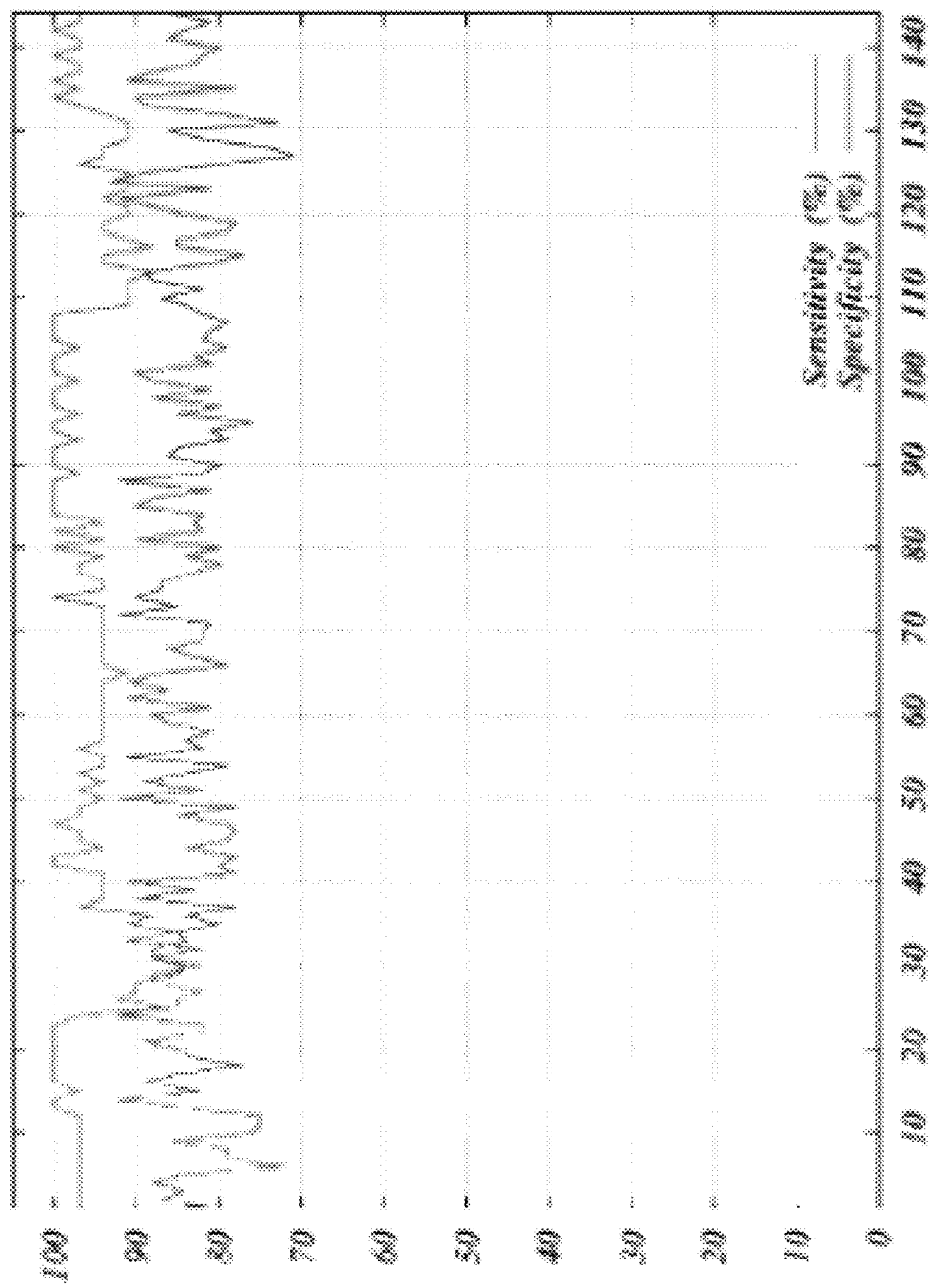
FIG. 12 shows sensitivity (red) and specificity (blue) for 144 different randomly drawn training and validation sets each consisting of 267 lesions.

FIG. 12 shows the performance of the present binary classifiers for discriminating between malignant and benign lesions in a set of unselected ("all-comer") lesions, similar to that a Primary Care Provider (PCP) is faced with. In this case, each training and validation set includes 34 malignant lesions (as confirmed by biopsy) and 233 benign lesions (as confirmed by dermatoscopy). From FIG. 12, the sensitivity and specificity are estimated to be 0.95 and 0.85, respectively, so that Eq. (28) gives $$A = \frac{34 \times 0.95 + 233 \times 0.85}{34 + 233} = 0.86. \tag{32}$$

Since the occurrence rate of malignant lesions in an all-comer study is very low, the accuracy of our classifier is expected to be close to the value above of 0.86, which is much higher than the accuracy of a PCP. Thus, our final diagnostic indication tool can be considered as capable of providing a PCP with reliable, real-time decisions regarding melanoma referrals.

Example 2

Lesions from 296 patients were scanned prospectively using an OTD device of the invention. A total of 712 lesions from 2 referral sources were imaged. Clinically benign lesions from the skin of volunteers accounted for 415 lesions. These lesions were chosen on the basis of normal dermatoscopic patterns and the absence of melanoma-specific criteria. In addition, the patients reported no known change in the lesion or any symptoms, and most patients had undergone full-body photography that documented no change. Biopsies were not obtained for these lesions.

Clinically suspicious lesions accounted for the remaining 297 scans and were chosen on the basis of clinical and dermatoscopic findings.

The clinically suspicious lesions were removed in toto with a saucerization excision technique and sent for histopathologic processing and examination. Pathologic specimens were processed with hematoxylin-eosin staining and, when indicated, immunohistochemical staining with Melan-A. (One lesion was a seborrheic keratosis and did not undergo immunostaining.)

Two dermatopathologists independently reviewed all specimens and rendered the diagnoses. Prior to removal, three OTD image sets were obtained from each lesion. The time needed to acquire each set was less than 10 seconds.

The OTD device used comprises a spectral reflectance meter that records 30 spectral reflectance images (1 image set) that constitute 1 measurement of a lesion under examination. Images were recorded at 10 different wavelengths (365-880 nm) from multiple polar and azimuth angles of illumination and detection. The image sets were recorded on a digital video disc and processed independently for creation of physiologic-morphologic maps, as described below. Although dermatoscopic images were also obtained for each lesion, these images were not used in the analysis.

Established absorption and transmission spectra for known skin chromophores and mathematical modeling of skin reflectance were used in analyzing the images. The images from each set were used to derive physiologic-morphologic maps of the lesions for the following seven parameters: percentage of hemoglobin concentration, percentage of hemoglobin oxygenation, upper epidermal thickness, lower epidermal thickness, percentage of upper melanin concentration, percentage of lower melanin concentration, and percentage of keratin concentration. From each physiologic-morphologic map, an entropy value was calculated and cross-entropy values were calculated between different pairs of maps. The entropy value provides a measure of the disorder in any one of the maps, and the cross-entropy value provides a measure of the correlation between 2 different maps. In addition, from a single green image for a wavelength of 510 nm, the following 10 morphological parameters were generated: 1) size; 2) histogram width (providing a measure of inhomogeneity of the reflected intensity); 3) fractal dimension; 4) moment of inertia; 5) asphericity; 6) center distance (representing the physical distance between the geometrical center of the lesion and its center of mass of absorptance); 7) border length; 8) average darkness; 9) area divided by fractal dimension; and 10) border length divided by fractal dimension.

For the 7 physiologic-morphologic maps, 28 weights were assigned to the entropy and cross-entropy values, and 28 weights to their logarithms. Similarly, 10 weights were assigned to the 10 morphological parameters and 10 to their logarithms. Another 10 diagnostic parameters were derived from the 7 maps, giving a total of 86 assigned weights. An OTD indication algorithm of the invention was optimized on a clinical data set consisting of 1,495 lesion images collected in several clinical studies from 2005 to present. By comparing the OTD diagnosis of melanoma or nonmelanoma with pathology or dermatoscopy results obtained from clinical data from 712 lesions, an OTD indication algorithm of the present invention was optimized and developed.

A total of 712 lesions were imaged, including 415 clinically and dermatoscopically benign lesions, 217 clinically suspicious but histopathologically benign lesions, and 80 malignant lesions (64 melanomas, 13 basal cell carcinomas, and 3 squamous cell carcinomas). The developed OTD algorithm misdiagnosed 1 of the melanomas as benign (sensitivity, 99%). The OTD specificity for the dermatoscopically benign lesions was 93% (384/415); for the lesions that were clinically suspicious but histopathologically benign, the OTD specificity was 36% (78/217); and for all benign lesions included in the study, the OTD specificity was 73% (462/632).

In practice, the high sensitivity and specificity provided by the systems and methods of the invention can help primary care providers substantially reduce the number of referrals for dermatology consultation, excision, or biopsy.

What is claimed is:

1. A method for discriminating between benign and malignant skin lesions, the method comprising the steps of:
    generating an image of a skin lesion;
    performing relative reflectance calibration of the image;
    performing compression of the image;
    performing zooming of the image to create lesion and surrounding area masks;
    creating, for each of a plurality of physiological properties and morphological parameters, a spatial distribution map covering the area of the skin lesion from the image of the skin lesion;
    determining entropy values for each of the spatial distribution maps;
    determining cross entropy values between pairs of the spatial distribution maps;
    determining, from image, a plurality of morphological parameters;
    deriving, from the spatial distribution maps of physiological properties and morphological parameters, a plurality of additional diagnostic parameters;
    creating one or more diagnostic indices from a weighted sum of the entropy values, the cross entropy values, the plurality of morphological parameters, and the plurality of additional diagnostic parameters, using one or more weight vectors;
    determining for each of the one or more diagnostic indices, a reliability value for classification as benign and a reliability value for classification as malignant; and
    classifying the skin lesion as benign where the reliability value for classification as benign is greater than the reliability value for classification as malignant.

2. The method of claim 1 wherein the plurality of physiological properties and morphological parameters are selected from the group consisting of percentage of hemoglobin concentration; percentage of hemoglobin oxygenation; upper epidermal thickness; lower epidermal thickness; percentage of melanosome concentration in upper epidermis; percentage of melanosome concentration in lower epidermis; and percentage of keratin concentration.

3. The method of claim 1 wherein the morphological parameters are selected from the group consisting of size; histogram width; fractal dimension; moment of inertia; asphericity; center distance; border length; average darkness; area divided by fractal dimension; and border length divided by fractal dimension.

4. The method of claim 1 wherein the additional diagnostic parameters are selected from the group consisting of maximum value of melanin optical depth; architectural disorder; blood filling; angiogenesis; ratio of blood oxygenation in an area surrounding a lesion border; melanin contrast; blood contrast; high spatial Fourier-components of a map of total melanin optical depth over a lesion area; and entropy of contrast of the map of total melanin optical depth over the lesion area.

5. The method of claim 1 wherein the image undergoes relative calibration comprising measuring intensity of each pixel due to backscattering for a corresponding pixel from a target having a Lambert surface.

6. The method of claim 1 wherein the one or more weight vectors are determined using clustering analysis of a plurality of pigmented skin lesion images known to be benign or malignant.

7. The method of claim 6 further wherein the plurality of physiological properties and morphological parameters, the plurality of morphological parameters, and the plurality of additional diagnostic parameters constitute a set of generalized diagnostic parameters and the one or more weight vectors used in creating the one or more diagnostic indices comprises a generalized weight vector.

8. The method of claim 1 wherein the image of the skin lesion is generated by a dermatoscope.

9. The method of claim 1 wherein the image of the skin lesion is generated using an optical transfer diagnosis (OTD) system comprising a handheld OTD unit in communication with a computing device.

10. The method of claim 1 wherein the image of the skin lesion is generated using a smart phone.

11. The method of claim 1 wherein the image of the skin lesion is generated using a tablet.

12. The method of claim 1 wherein the image of the skin lesion is generated using a digital camera.

13. The method of claim 1 further comprising estimating noise using one or more additional images of the skin lesion.

* * * * *